United States Patent [19]

Sih

[11] 4,336,372
[45] Jun. 22, 1982

[54] 2-DECARBOXY-2-TETRAZOLYL-PG$_2$ COMPOUNDS

[75] Inventor: John C. Sih, Kalamazoo, Mich.

[73] Assignee: The Upjohn Company, Kalamazoo, Mich.

[21] Appl. No.: 85,617

[22] Filed: Oct. 17, 1979

Related U.S. Application Data

[62] Division of Ser. No. 26,066, Apr. 2, 1979, Pat. No. 4,243,611.

[51] Int. Cl.$^3$ .................. C07D 257/06; C07D 409/08; A61K 31/41
[52] U.S. Cl. .................................... 542/429; 424/269; 548/253

[58] Field of Search ........................................ 542/429

[56] References Cited

U.S. PATENT DOCUMENTS 3,932,389  1/1976  Johnson et al. ...................... 548/252
4,064,351 12/1977  Sakai et al. ......................... 542/426

Primary Examiner—David B. Springer
Attorney, Agent, or Firm—Lawrence T. Welch; Robert A. Armitage

[57]  ABSTRACT

The present invention provides novel 2-decarboxy-2-tetrazolyl-PG$_2$ compounds, methods for their preparation and pharmacological use for the induction of prostaglandin-like effect.

1 Claim, No Drawings

2-DECARBOXY-2-TETRAZOLYL-PG$_2$ COMPOUNDS

CROSS REFERENCE TO RELATED APPLICATIONS

The present application is a division of Ser. No. 026,066, filed Apr. 2, 1979, now U.S. Pat. No. 4,243,611 issued Jan. 6, 1981.

BACKGROUND OF THE INVENTION

The present invention relates to novel prostaglandin analogs. Particularly, these compounds are analogs of the prostaglandins wherein the C-20-C-19 position is unsaturated, i.e., 19,20-didehydroPG compounds. Most particularly, the present invention relates to novel 2-decarboxy-2-tetrazolyl-PG$_2$ compounds, a disclosure of the preparation and use of which is incorporated here by reference from United States Ser. No. 025,899, filed Apr. 2, 1979, now U.S. Pat. No. 4,228,104 issued Oct. 14, 1980.

Prior Art

Prostaglandin analogs exhibiting unsaturation in the C-17, C-18, or C-20 position are known in the art. See, for example, U.S. Pat. No. 3,919,285 German Offenlegungsschrift No. 2,635,985 (and its corresponding Derwent Farmdoc CPI No. 10302A), and U.S. Pat. No. 4,064,351 for examples of such compounds. See also the references cited in U.S. Ser. No. 026,066.

SUMMARY OF THE INVENTION

The present invention particularly provides:
A compound of the formula

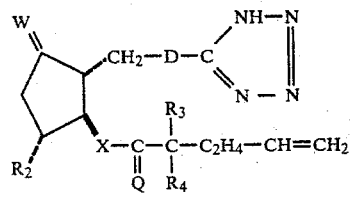

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—,
wherein Q is

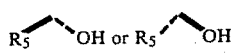

wherein g is zero, one, 2, or 3,
wherein R$_5$ is hydrogen or methyl,
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is

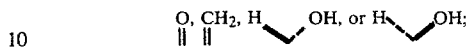

and wherein X is cis— or trans—CH=CH— or —C≡C—.

The compounds of the present invention are particularly useful for inducing prostaglandin-like biological effects, as is described in U.S. Ser. No. 026,066. Uses of compounds in accordance with the present invention include, therefore, anti-asthmatic indication.

I claim:
1. A compound of the formula

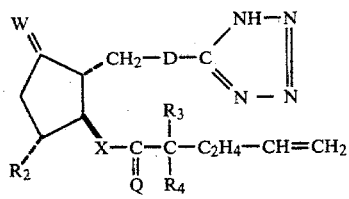

wherein D is
(1) cis—CH=CH—CH$_2$—(CH$_2$)$_g$—CH$_2$—,
(2) cis—CH=CH—CH$_2$—(CH$_2$)$_g$—CF$_2$—,
(3) cis—CH$_2$—CH=CH—CH$_2$—CH$_2$—,
(4) trans—(CH$_2$)$_3$—CH=CH—,
wherein Q is

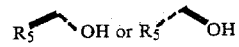

wherein g is zero, one, 2, or 3,
wherein R$_5$ is hydrogen or methyl,
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is

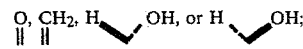

and wherein X is cis— or trans—CH=CH— or —C≡C—.

* * * * *